United States Patent
Zinger et al.

(10) Patent No.: US 8,435,210 B2
(45) Date of Patent: May 7, 2013

(54) FLUID CONTROL DEVICE WITH MANUALLY DEPRESSED ACTUATOR

(75) Inventors: Freddy Zinger, Ra'anana (IL); Igor Denenburg, Beberi (LV)

(73) Assignee: Medimop Medical Projects Ltd., Ra'anana (IL)

( * ) Notice: Subject to any disclaimer, the term of this patent is extended or adjusted under 35 U.S.C. 154(b) by 575 days.

(21) Appl. No.: 12/596,167

(22) PCT Filed: Apr. 16, 2008

(86) PCT No.: PCT/IL2008/000517
§ 371 (c)(1),
(2), (4) Date: Jan. 14, 2010

(87) PCT Pub. No.: WO2008/126090
PCT Pub. Date: Oct. 23, 2008

(65) Prior Publication Data
US 2010/0168664 A1    Jul. 1, 2010

(30) Foreign Application Priority Data
Apr. 17, 2007 (IL) .......................................... 182605

(51) Int. Cl.
*A61M 37/00* (2006.01)
(52) U.S. Cl.
USPC .......................................................... 604/82
(58) Field of Classification Search ................... 604/519
See application file for complete search history.

(56) References Cited

U.S. PATENT DOCUMENTS

| 62,333 | A | 2/1867 | Holl |
| 1,704,817 | A | 3/1929 | Ayers |
| 1,930,944 | A | 10/1933 | Schmitz, Jr. |
| 2,326,490 | A | 8/1943 | Perelson |
| 2,931,668 | A | 4/1960 | Baley |
| 2,968,497 | A | 1/1961 | Treleman |
| 3,059,643 | A | 10/1962 | Barton |

(Continued)

FOREIGN PATENT DOCUMENTS

| DE | 4122476 A1 | 1/1993 |
| DE | 19504413 A1 | 8/1996 |

(Continued)

OTHER PUBLICATIONS

Office Action issued Nov. 12, 2010 in U.S. Appl. No. 29/334,697.

(Continued)

*Primary Examiner* — Nicholas Lucchesi
*Assistant Examiner* — Weng Lee
(74) *Attorney, Agent, or Firm* — Panitch Schwarze Belisario & Nadel LLP (57) ABSTRACT

Fluid control device (70) including a housing (31) with a syringe port (33) for receiving a syringe, a vial adapter port (36) with a vial adapter (86) for snap fit receiving a vial, and a drug administration port (34) for administering a liquid drug. The vial adapter is intended to be rotationally detached after a mixing procedure for discarding together with a spent vial. The fluid control device additionally includes a manually depressed actuator (74) for sealing pathways which may lead to leakage of liquid drug subsequent to vial adapter detachment, thereby facilitating their use for handling and administration of hazardous liquid drugs. The manually depressed actuator preferably precludes vial adapter detachment prior to actuation, thereby ensuring failsafe operation.

5 Claims, 6 Drawing Sheets

U.S. PATENT DOCUMENTS

| | | |
|---|---|---|
| D198,499 S | 6/1964 | Harautuneian |
| 3,484,849 A | 12/1969 | Huebner et al. |
| 3,618,637 A | 11/1971 | Santomieri |
| 3,757,981 A | 9/1973 | Harris, Sr. et al. |
| 3,826,261 A | 7/1974 | Killinger |
| 3,885,607 A | 5/1975 | Peltier |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,051,852 A | 10/1977 | Villari |
| 4,109,670 A | 8/1978 | Slagel |
| 4,187,848 A | 2/1980 | Taylor |
| 4,210,173 A | 7/1980 | Choksi et al. |
| D257,286 S | 10/1980 | Folkman |
| 4,253,501 A | 3/1981 | Ogle |
| 4,296,786 A | 10/1981 | Brignola |
| 4,314,586 A | 2/1982 | Folkman |
| 4,328,802 A | 5/1982 | Curley et al. |
| D267,199 S | 12/1982 | Koenig |
| 4,376,634 A | 3/1983 | Prior et al. |
| D271,421 S | 11/1983 | Fetterman |
| 4,434,823 A | 3/1984 | Hudspith |
| 4,475,915 A | 10/1984 | Sloane |
| 4,493,348 A | 1/1985 | Lemmons |
| 4,505,709 A | 3/1985 | Froning et al. |
| 4,507,113 A | 3/1985 | Dunlap |
| D280,018 S | 8/1985 | Scott |
| 4,532,969 A | 8/1985 | Kwaan |
| 4,564,054 A | 1/1986 | Gustavsson |
| 4,576,211 A | 3/1986 | Valentini et al. |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,676,530 A | 6/1987 | Nordgren et al. |
| 4,697,622 A | 10/1987 | Swift et al. |
| 4,721,133 A | 1/1988 | Sundblom |
| 4,729,401 A | 3/1988 | Raines |
| 4,743,229 A | 5/1988 | Chu |
| 4,743,243 A | 5/1988 | Vaillancourt |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,834,152 A | 5/1989 | Howson et al. |
| 4,865,592 A | 9/1989 | Rycroft |
| 4,909,290 A | 3/1990 | Coccia |
| 4,967,797 A | 11/1990 | Manska |
| D314,050 S | 1/1991 | Sone |
| 4,997,430 A | 3/1991 | Van der Heiden et al. |
| 5,035,686 A | 7/1991 | Crittenden et al. |
| 5,041,105 A | 8/1991 | D'Alo et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,171,230 A | 12/1992 | Eland et al. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| 5,232,109 A | 8/1993 | Tirrell et al. |
| 5,247,972 A | 9/1993 | Tetreault |
| 5,269,768 A | 12/1993 | Cheung |
| 5,270,219 A | 12/1993 | DeCastro et al. |
| 5,279,576 A | 1/1994 | Loo et al. |
| 5,288,290 A | 2/1994 | Brody |
| 5,304,163 A | 4/1994 | Bonnici et al. |
| 5,312,377 A | 5/1994 | Dalton |
| 5,328,474 A | 7/1994 | Raines |
| 5,334,163 A | 8/1994 | Sinnett |
| 5,342,346 A | 8/1994 | Honda et al. |
| 5,344,417 A | 9/1994 | Wadsworth, Jr. |
| 5,350,372 A | 9/1994 | Ikeda et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| 5,445,630 A | 8/1995 | Richmond |
| 5,445,631 A | 8/1995 | Uchida |
| 5,464,123 A | 11/1995 | Scarrow |
| 5,466,219 A | 11/1995 | Lynn et al. |
| 5,466,220 A | 11/1995 | Brenneman |
| 5,478,337 A | 12/1995 | Okamoto et al. |
| 5,492,147 A | 2/1996 | Challender et al. |
| 5,505,714 A | 4/1996 | Dassa et al. |
| 5,509,433 A | 4/1996 | Paradis |
| 5,520,659 A | 5/1996 | Hedges |
| 5,526,853 A | 6/1996 | McPhee et al. |
| 5,531,695 A | 7/1996 | Swisher |
| 5,554,128 A | 9/1996 | Hedges |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley, III et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,641,010 A | 6/1997 | Maier |
| 5,647,845 A | 7/1997 | Haber et al. |
| 5,651,776 A | 7/1997 | Appling et al. |
| 5,653,686 A | 8/1997 | Coulter et al. |
| 5,674,195 A | 10/1997 | Truthan |
| 5,718,346 A | 2/1998 | Weiler |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,755,696 A | 5/1998 | Caizza |
| 5,772,630 A | 6/1998 | Ljungquist |
| 5,772,652 A | 6/1998 | Zielinski |
| RE35,841 E | 7/1998 | Frank et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,893,397 A | 4/1999 | Peterson et al. |
| 5,919,182 A | 7/1999 | Avallone |
| 5,925,029 A | 7/1999 | Jansen et al. |
| 5,944,700 A | 8/1999 | Nguyen et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,063,068 A | 5/2000 | Fowles et al. |
| D427,308 S | 6/2000 | Zinger |
| 6,080,132 A | 6/2000 | Cole et al. |
| 6,090,093 A | 7/2000 | Thibault et al. |
| 6,099,511 A | 8/2000 | Devos et al. |
| 6,113,583 A | 9/2000 | Fowles et al. |
| 6,139,534 A | 10/2000 | Niedospial, Jr. et al. |
| 6,142,446 A | 11/2000 | Leinsing |
| 6,156,025 A | 12/2000 | Niedospial, Jr. et al. |
| 6,159,192 A | 12/2000 | Fowles et al. |
| 6,171,293 B1 | 1/2001 | Rowley et al. |

| | | |
|---|---|---|
| 6,174,304 B1 | 1/2001 | Weston |
| 6,221,041 B1 | 4/2001 | Russo |
| 6,221,054 B1 | 4/2001 | Martin et al. |
| 6,238,372 B1 | 5/2001 | Zinger et al. |
| 6,245,044 B1 | 6/2001 | Daw et al. |
| D445,501 S | 7/2001 | Niedospial, Jr. |
| 6,253,804 B1 | 7/2001 | Safabash |
| 6,258,078 B1 | 7/2001 | Thilly |
| 6,280,430 B1 | 8/2001 | Neftel et al. |
| 6,343,629 B1 | 2/2002 | Wessman et al. |
| 6,348,044 B1 | 2/2002 | Coletti et al. |
| 6,358,236 B1 | 3/2002 | DeFoggi et al. |
| 6,379,340 B1 | 4/2002 | Zinger et al. |
| 6,408,897 B1 | 6/2002 | Laurent et al. |
| 6,409,708 B1 | 6/2002 | Wessman |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,503,240 B1 | 1/2003 | Niedospial, Jr. et al. |
| 6,503,244 B2 | 1/2003 | Hayman |
| 6,524,278 B1 | 2/2003 | Campbell et al. |
| D472,316 S | 3/2003 | Douglas et al. |
| 6,530,903 B2 | 3/2003 | Wang et al. |
| D472,630 S | 4/2003 | Douglas et al. |
| 6,544,246 B1 | 4/2003 | Niedospial, Jr. |
| 6,551,299 B2 | 4/2003 | Miyoshi et al. |
| 6,558,365 B2 | 5/2003 | Zinger et al. |
| 6,572,591 B2 | 6/2003 | Mayer |
| 6,575,955 B2 | 6/2003 | Azzolini |
| 6,581,593 B1 | 6/2003 | Rubin et al. |
| 6,582,415 B1 | 6/2003 | Fowles et al. |
| 6,591,876 B2 | 7/2003 | Safabash |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial, Jr. |
| 6,681,810 B2 | 1/2004 | Weston |
| 6,681,946 B1 | 1/2004 | Jansen et al. |
| 6,695,829 B2 | 2/2004 | Hellstrom et al. |
| 6,699,229 B2 | 3/2004 | Zinger et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Arnissolle |
| 6,752,180 B2 | 6/2004 | Delay |
| D495,416 S | 8/2004 | Dimeo et al. |
| D496,457 S | 9/2004 | Prais et al. |
| 6,832,994 B2 | 12/2004 | Niedospial, Jr. et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,890,328 B2 | 5/2005 | Fowles et al. |
| 6,901,975 B2 | 6/2005 | Aramata et al. |
| 6,949,086 B2 | 9/2005 | Ferguson et al. |
| RE38,996 E | 2/2006 | Crawford et al. |
| 6,994,315 B2 | 2/2006 | Ryan et al. |
| 6,997,917 B2 | 2/2006 | Niedospial, Jr. et al. |
| 7,024,968 B2 | 4/2006 | Raudabough et al. |
| 7,074,216 B2 | 7/2006 | Fowles et al. |
| 7,083,600 B2 | 8/2006 | Meloul |
| 7,150,735 B2 | 12/2006 | Hickle |
| 7,192,423 B2 | 3/2007 | Wong |
| 7,294,122 B2 | 11/2007 | Kubo et al. |
| D561,348 S | 2/2008 | Zinger et al. |
| 7,326,194 B2 | 2/2008 | Zinger et al. |
| 7,350,764 B2 | 4/2008 | Raybuck |
| 7,354,422 B2 | 4/2008 | Riesenberger et al. |
| 7,354,427 B2 | 4/2008 | Fangrow |
| 7,425,209 B2 | 9/2008 | Fowles et al. |
| 7,435,246 B2 | 10/2008 | Zihlmann |
| 7,452,348 B2 | 11/2008 | Hasegawa |
| 7,470,265 B2 | 12/2008 | Brugger et al. |
| 7,488,297 B2 | 2/2009 | Flaherty |
| 7,491,197 B2 | 2/2009 | Jansen et al. |
| 7,523,967 B2 | 4/2009 | Steppe |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| D595,862 S | 7/2009 | Suzuki et al. |
| D595,863 S | 7/2009 | Suzuki et al. |
| 7,611,487 B2 | 11/2009 | Woehr et al. |
| 7,611,502 B2 | 11/2009 | Daly |
| 7,628,779 B2 | 12/2009 | Aneas |
| 7,632,261 B2 | 12/2009 | Zinger et al. |
| 7,654,995 B2 | 2/2010 | Warren et al. |
| 7,695,445 B2 | 4/2010 | Yuki |
| D616,090 S | 5/2010 | Kawamura |
| 7,722,090 B2 | 5/2010 | Burton et al. |
| D616,984 S | 6/2010 | Gilboa |
| 7,731,678 B2 * | 6/2010 | Tennican et al. .............. 604/88 |
| 7,743,799 B2 | 6/2010 | Mosler et al. |
| 7,758,082 B2 | 7/2010 | Weigel et al. |
| 7,771,383 B2 | 8/2010 | Truitt et al. |
| 7,799,009 B2 | 9/2010 | Niedospial, Jr. et al. |
| 7,803,140 B2 | 9/2010 | Fangrow, Jr. |
| D630,732 S | 1/2011 | Lev et al. |
| 7,879,018 B2 | 2/2011 | Zinger et al. |
| 7,900,659 B2 | 3/2011 | Whitley et al. |
| D637,713 S | 5/2011 | Nord et al. |
| 2001/0029360 A1 | 10/2001 | Miyoshi et al. |
| 2001/0051793 A1 | 12/2001 | Weston |
| 2002/0017328 A1 | 2/2002 | Loo |
| 2002/0066715 A1 | 6/2002 | Niedospial |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0121496 A1 | 9/2002 | Thiebault et al. |
| 2002/0123736 A1 | 9/2002 | Fowles et al. |
| 2002/0127150 A1 | 9/2002 | Sasso |
| 2002/0173752 A1 | 11/2002 | Polzin |
| 2002/0193777 A1 | 12/2002 | Aneas |
| 2003/0036725 A1 | 2/2003 | Lavi et al. |
| 2003/0100866 A1 | 5/2003 | Reynolds |
| 2003/0120209 A1 | 6/2003 | Jensen et al. |
| 2003/0153895 A1 | 8/2003 | Leinsing |
| 2003/0195479 A1 | 10/2003 | Kuracina et al. |
| 2003/0199846 A1 | 10/2003 | Fowles et al. |
| 2003/0199847 A1 | 10/2003 | Akerlund et al. |
| 2004/0024354 A1 | 2/2004 | Reynolds |
| 2004/0044327 A1 | 3/2004 | Hasegawa |
| 2004/0073189 A1 | 4/2004 | Wyatt et al. |
| 2004/0153047 A1 | 8/2004 | Blank et al. |
| 2004/0181192 A1 | 9/2004 | Cuppy |
| 2004/0217315 A1 | 11/2004 | Doyle |
| 2004/0236305 A1 | 11/2004 | Jansen et al. |
| 2005/0124964 A1 | 6/2005 | Niedospial et al. |
| 2005/0137566 A1 | 6/2005 | Fowles et al. |
| 2005/0148994 A1 | 7/2005 | Leinsing |
| 2006/0030832 A1 | 2/2006 | Niedospial et al. |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0106360 A1 | 5/2006 | Wong |
| 2006/0135948 A1 | 6/2006 | Varma |
| 2006/0253084 A1 | 11/2006 | Nordgren |
| 2007/0060904 A1 | 3/2007 | Vedrine et al. |
| 2007/0079894 A1 | 4/2007 | Kraus et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0106244 A1 | 5/2007 | Mosler et al. |
| 2007/0156112 A1 | 7/2007 | Walsh |
| 2007/0167904 A1 | 7/2007 | Zinger et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0219483 A1 | 9/2007 | Kitani et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0255202 A1 | 11/2007 | Kitani et al. |

| | | | |
|---|---|---|---|
| 2007/0265574 A1 | 11/2007 | Tennican et al. | |
| 2007/0265581 A1 | 11/2007 | Funamura et al. | |
| 2007/0270778 A9 | 11/2007 | Zinger et al. | |
| 2007/0287953 A1 | 12/2007 | Ziv et al. | |
| 2008/0009789 A1 | 1/2008 | Zinger et al. | |
| 2008/0172024 A1 | 7/2008 | Yow | |
| 2008/0249479 A1 | 10/2008 | Zinger et al. | |
| 2008/0249498 A1 | 10/2008 | Fangrow | |
| 2008/0312634 A1 | 12/2008 | Helmerson et al. | |
| 2009/0012492 A1 | 1/2009 | Zihlmann | |
| 2009/0054834 A1 | 2/2009 | Zinger et al. | |
| 2009/0082750 A1 | 3/2009 | Denenburg et al. | |
| 2009/0143758 A1 | 6/2009 | Okiyama | |
| 2009/0177177 A1 | 7/2009 | Zinger et al. | |
| 2009/0177178 A1 | 7/2009 | Pedersen | |
| 2009/0187140 A1 | 7/2009 | Racz | |
| 2009/0216212 A1 | 8/2009 | Fangrow, Jr. | |
| 2009/0299325 A1 | 12/2009 | Vedrine et al. | |
| 2009/0326506 A1 | 12/2009 | Hasegawa et al. | |
| 2010/0010443 A1 | 1/2010 | Morgan et al. | |
| 2010/0030181 A1 | 2/2010 | Helle et al. | |
| 2010/0036319 A1 | 2/2010 | Drake et al. | |
| 2010/0076397 A1 | 3/2010 | Reed et al. | |
| 2010/0087786 A1 | 4/2010 | Zinger et al. | |
| 2010/0137827 A1 | 6/2010 | Warren et al. | |
| 2010/0179506 A1 | 7/2010 | Shemesh et al. | |
| 2010/0204670 A1 | 8/2010 | Kraushaar et al. | |
| 2010/0228220 A1 | 9/2010 | Zinger et al. | |
| 2010/0241088 A1 | 9/2010 | Ranalletta et al. | |
| 2010/0286661 A1 | 11/2010 | Raday et al. | |
| 2010/0312220 A1 | 12/2010 | Kalitzki | |
| 2011/0230856 A1 | 9/2011 | Kyle et al. | |
| 2011/0264069 A1 | 10/2011 | Bochenko | |
| 2011/0276007 A1 | 11/2011 | Denenburg | |

FOREIGN PATENT DOCUMENTS

| | | |
|---|---|---|
| DE | 202004012714 U1 | 11/2004 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0518397 A1 | 12/1992 |
| EP | 0521460 A1 | 1/1993 |
| EP | 0637443 A1 | 2/1995 |
| EP | 0737467 A1 | 10/1996 |
| EP | 0806597 A1 | 11/1997 |
| EP | 0814866 A1 | 1/1998 |
| EP | 0898951 A2 | 3/1999 |
| EP | 1008337 A1 | 6/2000 |
| EP | 1051988 A2 | 11/2000 |
| EP | 1329210 A1 | 7/2003 |
| EP | 1454609 A1 | 9/2004 |
| EP | 1454650 A1 | 9/2004 |
| EP | 1 498 097 A2 | 1/2005 |
| EP | 1872824 A1 | 1/2008 |
| EP | 1919432 A1 | 5/2008 |
| EP | 1930038 A2 | 6/2008 |
| FR | 2029242 A5 | 10/1970 |
| FR | 2869795 A1 | 11/2005 |
| GB | 1444210 A | 7/1976 |
| JP | 4329954 A | 11/1992 |
| JP | 11503627 T | 3/1999 |
| JP | 2003-102807 A | 4/2003 |
| WO | 1913926 A1 | 9/1970 |
| WO | 9403373 A1 | 2/1994 |
| WO | 9507066 A1 | 3/1995 |
| WO | 9629113 A1 | 9/1996 |
| WO | 9600053 A1 | 10/1996 |
| WO | 9832411 A1 | 7/1998 |
| WO | 9837854 A1 | 9/1998 |
| WO | 1029526 A1 | 8/2000 |
| WO | 0128490 A1 | 4/2001 |
| WO | 0130425 A1 | 5/2001 |
| WO | 0132524 A1 | 5/2001 |
| WO | 0160311 A1 | 8/2001 |
| WO | 0191693 A2 | 12/2001 |
| WO | 0209797 A1 | 2/2002 |
| WO | 03051423 A2 | 6/2003 |
| WO | 2004041148 A1 | 5/2004 |
| WO | 2005105014 A2 | 11/2005 |
| WO | 2007/015233 A1 | 2/2007 |
| WO | 2007017868 A1 | 2/2007 |
| WO | 2007105221 A1 | 9/2007 |
| WO | 2009026443 A2 | 2/2009 |
| WO | 2009029010 A1 | 3/2009 |
| WO | 2009038860 A2 | 3/2009 |
| WO | 2009040804 A2 | 4/2009 |
| WO | 2009087572 A1 | 7/2009 |
| WO | 2009093249 A1 | 7/2009 |
| WO | 2009112489 A1 | 9/2009 |

OTHER PUBLICATIONS

The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued Mar. 6, 2012 in Int'l Application No. PCT/IL2011/000834; Written Opinion.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 2008801108283.4.
Office Action issued Mar. 6, 2012 in U.S. Appl. No. 12/678,928.
Int'l Search Report issued Feb. 3, 2011 in Int'l Application No. PCT/IL2010/000777.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
http://www.westpharma.com/eu/en/products/Pages/Mixject.aspx.
Int'l Search Report issued Oct. 7, 2011 in Int'l Application No. PCT/IL2011/000511.
U.S. Appl. No. 13/498,378 by LEV, filed Mar. 27, 2012.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
U.S. Appl. No. 13/505,790 by LEV, filed May 3, 2012.
U.S. Appl. No. 13/505,881 by LEV, filed May 3, 2012.
http://www.westpharma.com/eu/SiteCollectionDocuments/Recon/mixject%20product%20sheet.pfg; Mixject product information sheet pp. 1.
Written Opinion of ISR Issued in Int'l Application No. PCT/IL2005/000376.
Written Opinion of the ISR Issued in Int'l Application No. PCT/IL08/00517.

Int'l Search Report issued Aug. 16, 2012 in Int'l Application No. PCT/IL2012/000164.
U.S. Appl. No. 13/522,410 by LEV, filed Jul. 16, 2012.
U.S. Appl. No. 13/576,461 by LEV, filed Aug. 1, 2012.
Office Action issued Jun. 14, 2012 in U.S. Appl. No. 29/376,980.
Office Action issued Jun. 15, 2012 in U.S. Appl. No. 29/413,170.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle Systems, Alaris Medical Systems Webpage, 4 pages, Feb. 2006.
Photographs of Alaris Medical Systems SmartSite.RTM. device, 5 pages, 2002.
Non-Vented Vial Access Pin with Ultrasite.RTM. Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/SiteCollectionDocuments/Recon/mixject%20product%20sheet.pfg: Mixject product information sheet pp. 1.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376, Oct. 29, 2006.
Int'l Search Report Issued Aug. 25, 2008 in Int'l Application No. PCT/IL2008/000517.
Written Opinion of the ISR Issued in Int'l Application No. PCT/IL08/00517, Oct. 17, 2009.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
U.S. Appl. No. 29/438,134 by Lev, filed Nov. 27, 2012.
U.S. Appl. No. 29/438,141 by Gilboa, filed Nov. 27, 2012.

* cited by examiner

FLUID CONTROL DEVICE WITH MANUALLY DEPRESSED ACTUATOR

CROSS-REFERENCE TO RELATED APPLICATION

This application is a Section 371 of International Application No. PCT/IL2008/000517, filed Apr. 16, 2008, which was published in the English language on Oct. 23, 2008 under International Publication No. WO 2008/126090 A1, and the disclosure of which is incorporated herein by reference.

BACKGROUND OF THE INVENTION

Drugs for the treatment of cancer, cytostatics, and the like, constitute serious health risks to pharmacy staff and oncology nurses that handle and administer them. Carmel Pharma AB, Sweden have developed a range of drug delivery systems commercially available under the registered trademark PhaSeal® for the handling and administration of hazardous liquid drugs. PhaSeal® delivery systems can be viewed online at www.phaseal.com.

Commonly owned PCT International Application No. PCT/IL2006/000881 entitled Liquid Drug delivery System and published under PCT International Publication No. WO 2007/015233 illustrates and describes a liquid drug delivery system for sterile or aseptic handling.

Commonly owned U.S. Pat. No. 6,238,372 to Zinger et al., the contents of which are incorporated herein by reference, illustrates and describes fluid control devices for administration of liquid drugs. U.S. '372 FIGS. 1 to 19 illustrate fluid control devices including a housing with a syringe port for receiving a syringe, a vial adapter port with a vial adapter for snap fit receiving a vial, and a drug administration port for administering a liquid drug.

U.S. '372 FIGS. 11 to 15 illustrate fluid control devices having vial adapter ports with vial adapters intended to be rotationally detached after a mixing procedure whereupon the detached vial adapters are intended to be discarded together with spent vials. Such fluid control devices are commercially available under the registered trademark MIXJECT® from Medimop Medical Projects Ltd., Ra'anana, Israel. MIXJECT® product information is available at http://www.westpharma.com/products/medimop/Information/mixject.pdf. However, vial adapter detachment leaves open pathways which may lead to leakage of residual liquid drug thereby posing a possible health risk in the case of mixing of hazardous liquid drugs.

SUMMARY OF THE INVENTION

The present invention is directed to novel fluid control devices having a similar construction and operation as aforesaid U.S. '372 FIGS. 11 to 15's fluid control devices and additionally including a manually depressed actuator for sealing pathways which may lead to leakage of liquid drug subsequent to vial adapter detachment, thereby facilitating their use for handling and administration of hazardous liquid drugs. Moreover, the manually depressed actuator preferably precludes vial adapter detachment prior to actuation, thereby ensuring failsafe operation.

BRIEF DESCRIPTION OF THE DRAWINGS

In order to understand the invention and to see how it can be carried out in practice, a preferred embodiment will now be described, by way of a non-limiting example only, with reference to the accompanying drawings in which similar parts are likewise numbered, and in which.

DESCRIPTION OF PREFERRED EMBODIMENT OF THE INVENTION

Figure 1:
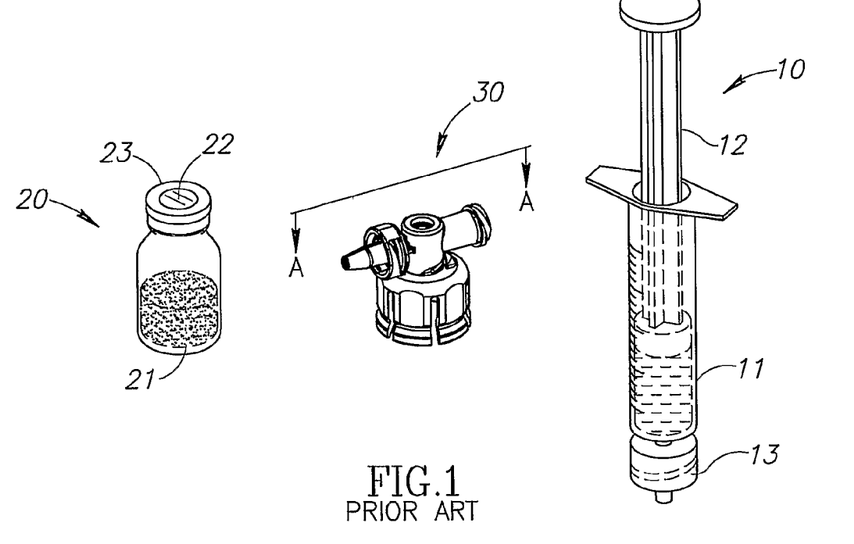
FIG. 1 is a pictorial representation of a syringe, a vial, and a fluid control device according to U.S. Pat. No. 6,238,372's FIGS. 11 to 15.

FIG. 1 shows a syringe 10, a vial 20, and a fluid control device 30 for liquid drug mixing and administration purposes. The syringe 10 includes a barrel 11 with a plunger 12, and a male Luer lock connector 13. The vial 20 includes an opened topped bottle 21 sealed by a rubber stopper 22 capped by a metal band 23. The syringe 10 typically includes a diluent for either reconstituting a powder drug or mixing with a liquid drug contained in the vial 20.

Figure 2:
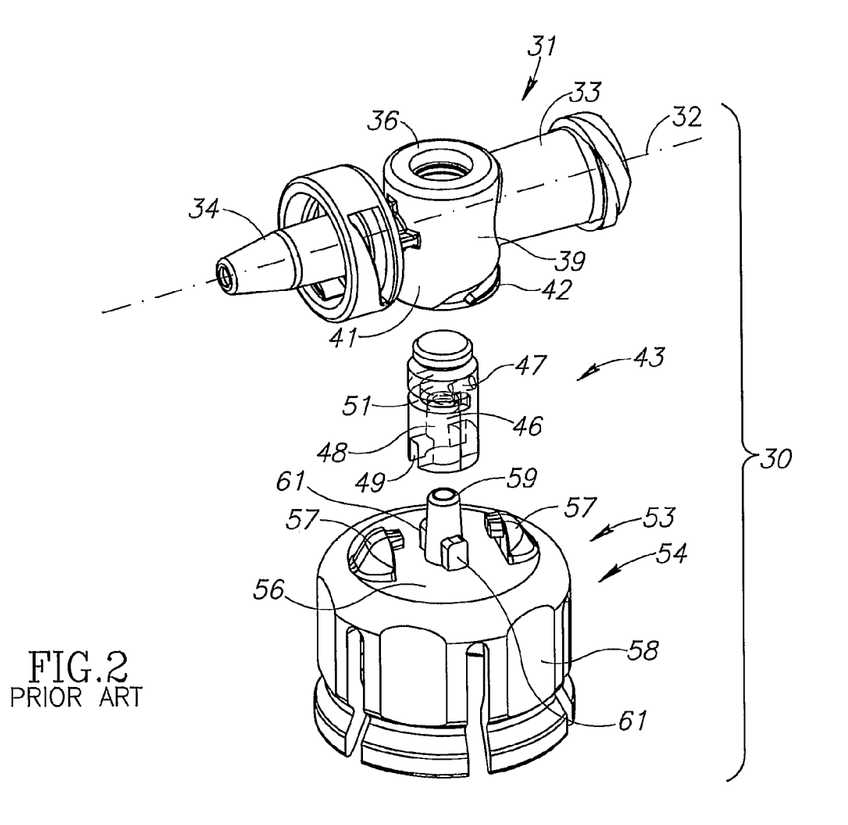
FIG. 2 is an exploded view of FIG. 1's fluid control device.
Figure 3:
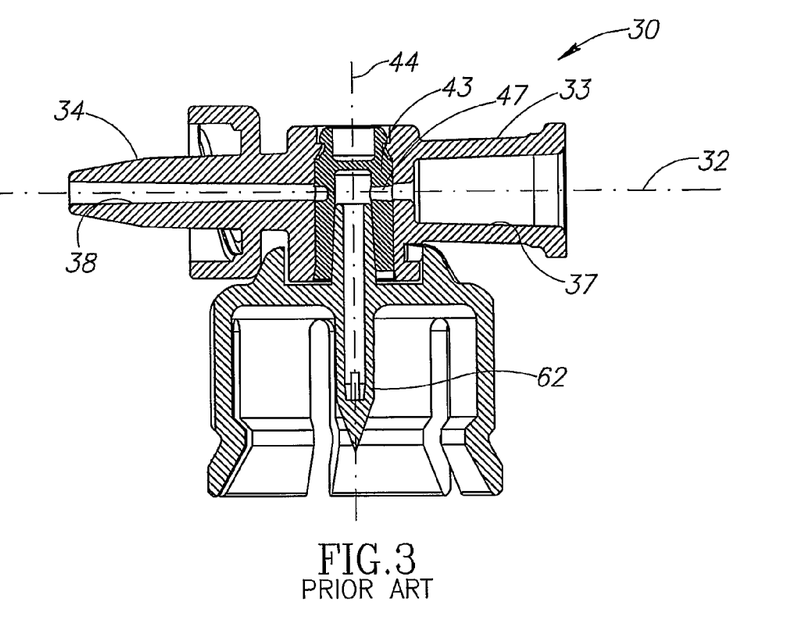
FIG. 3 is a longitudinal cross section of FIG. 1's fluid control device along line A-A in FIG. 1 in a mixing flow control position.
Figure 4:
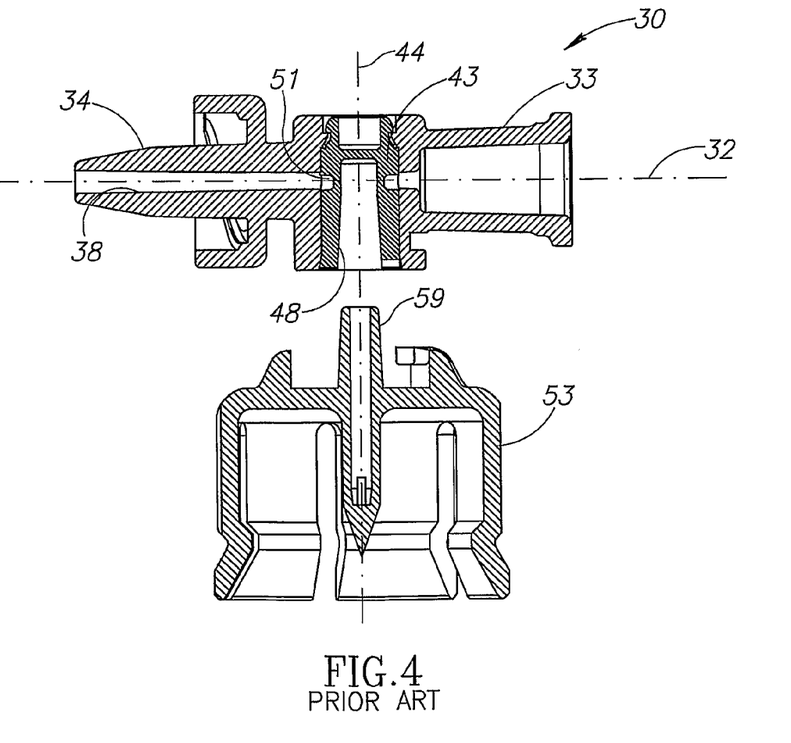
FIG. 4 is a longitudinal cross section of FIG. 1's fluid control device along line A-A in FIG. 1 in an administration flow control position subsequent to vial adapter detachment.

FIGS. 2 to 4 show the fluid control device 30 includes a housing 31 having a longitudinal axis 32, a syringe port 33 and a drug administration port 34 co-directional with the longitudinal axis 32, and a tubular vial adapter port 36 intermediate the syringe port 33 and the drug administration port 34. The syringe port 33 includes a lumen 37 in flow communication with the vial adapter port 36 and slidingly receiving a syringe 10. The drug administration port 34 includes a lumen 38 in flow communication with the vial adapter port 36 and intended for administrating a liquid drug.

The vial adapter port 36 has an outer cylindrical surface 39 with a lowermost portion 41 having a pair of opposite quarter turn screw threads 42. The vial adapter port 36 supports a flow control member 43 rotatable about an axis of rotation 44 generally perpendicular to the longitudinal axis 32. The flow control member 43 has an L-shaped mixing flow channel 46 including a radial section 47 for registration with the syringe port's lumen 37 in a mixing flow control position and an axial section 48 terminating in a diametrical slot 49. The flow control member 43 has a peripheral semi-circular administration flow channel 51 for registration with the syringe port's lumen 37 and the drug administration port's lumen 38 in an administration flow control position subsequent to a quarter turn with respect to its mixing flow control position.

The fluid control device 30 includes a vial adapter 53 with a skirt 54 for telescopically receiving a vial 20. The skirt 54 has a top surface 56 with a pair of opposite screw thread members 57 for screw thread engaging the screw threads 42 thereby coupling the vial adapter 53 to the housing 31, and six downward depending flex members 58 for snap fitting onto a vial 20. The vial adapter 53 includes an upright tapered hollow male connector 59 for sealing insertion into the flow control member's axial section 48 and a pair of keys 61 for insertion into the flow control member's slot 49 for coupling the vial adapter 53 to the flow control member 43. The vial adapter 53 includes a downward depending hollow cannula 62 for puncturing a vial's rubber stopper 22 and extending into a vial bottle 21's interior. The male connector 59 and the cannula 62 are in flow communication.

FIGS. 3 and 4 show the operation of the fluid control device 30:

FIG. 3 shows the fluid control device 30 with the vial adapter 53 coupled thereon and the flow control member 43 in its initial mixing flow control position enabling flow communication between a syringe inserted into the syringe port 33 and a vial inserted into the vial adapter 53. The diluent is injected into the vial for mixing with its contents prior to aspiration of the liquid drug into the syringe ready for administration.

FIG. 4 shows the fluid control device 30 subsequent to quarter turn rotation of the vial adapter 53 relative to the housing 31 for detaching the vial adapter 53 with a spent vial therefrom and simultaneously rotating the flow control member 43 from its initial mixing flow control position to its subsequent administration flow control position for enabling flow communication between the syringe port 33 and the drug administration port 34. Some liquid drug may remain in a vial 20 and spill out through the open male connector 59 and in the L-shaped mixing flow channel's radial section 47 (not seen in FIG. 4) and leak out through its axial section 48 which can pose a possible health risk in the case of hazardous liquid drugs.

Figure 5:
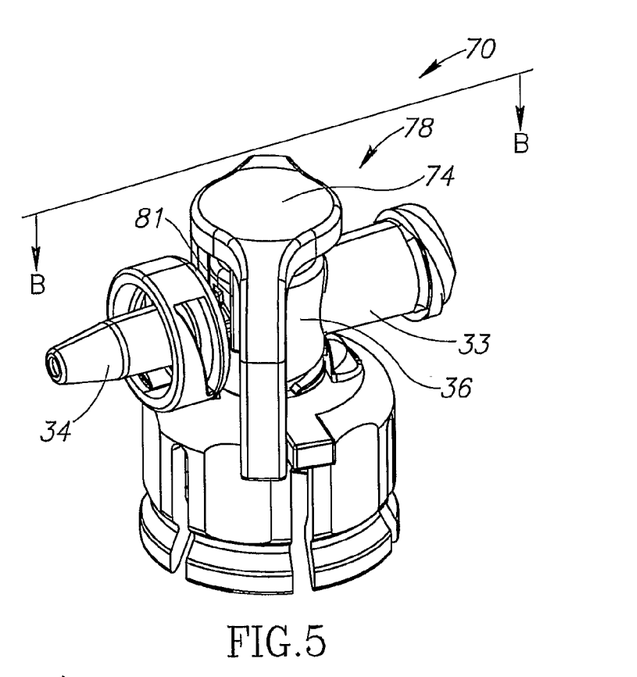
FIG. 5 is a perspective view of a fluid control device with a manually depressed actuator prior to actuation.
Figure 6:
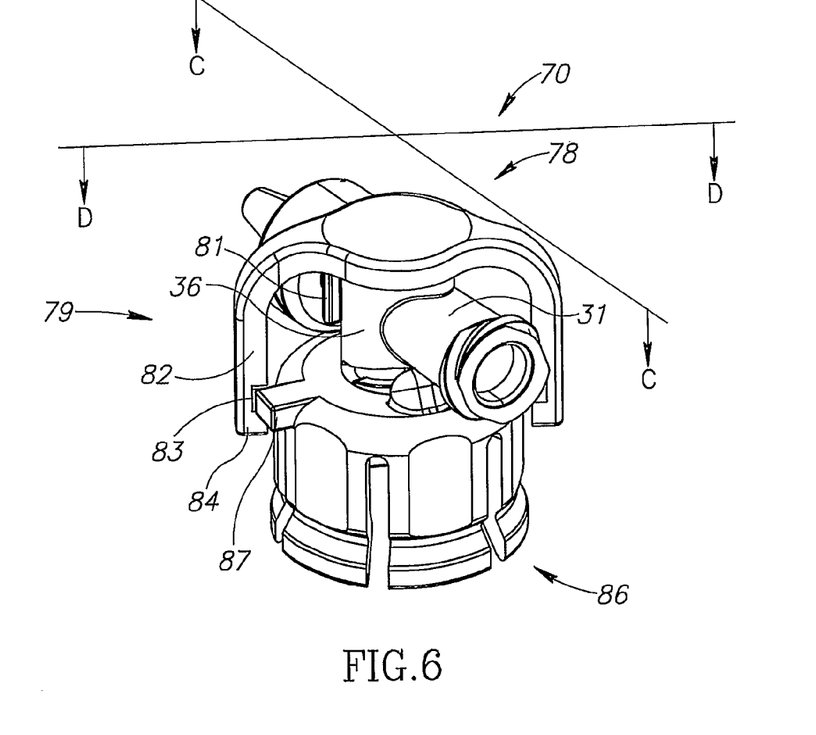
FIG. 6 is another perspective view of FIG. 5's fluid control device subsequent to actuation of its manually depressed actuator.
Figure 7:
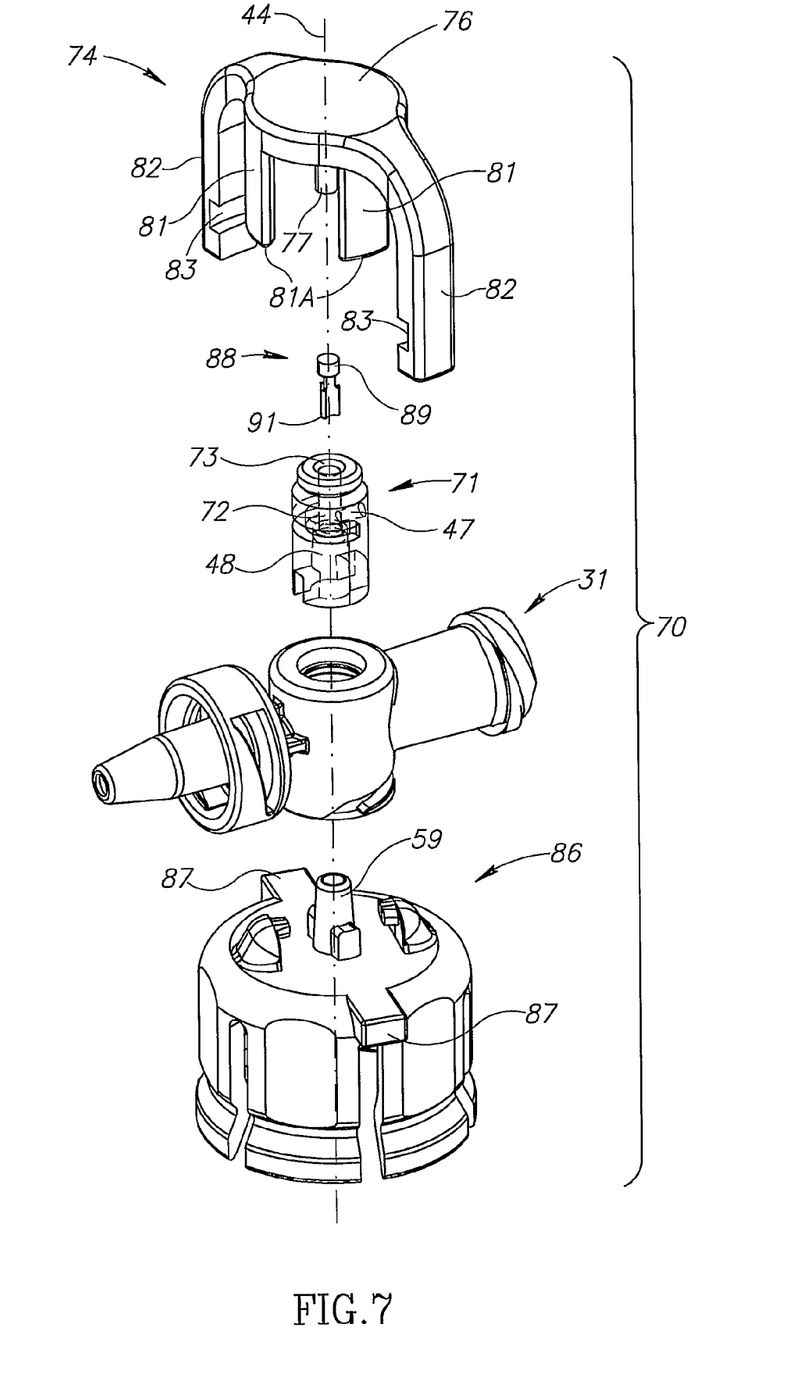
FIG. 7 is an exploded view of FIG. 5's fluid control device.

FIGS. 5 to 7 show a fluid control device 70 similar in construction to the fluid control device 30 and therefore similar parts are likewise numbered. The fluid control device 70 includes a flow control member 71 similar to the flow control member 43 but additionally including an axial extension 72 to the L-shaped mixing flow channel's axial section 48, thereby forming an axial throughgoing bore 73 co-axial with the axis of rotation 44.

The fluid control device 70 includes a manually depressed actuator 74 with a manually depressed head 76 having a downward depending shaft 77, an alignment mechanism 78 for fixedly aligning the manually depressed actuator 74 with respect to the housing 31 and a stopping mechanism 79 for enabling vial adapter detachment conditional on depression of the manually depressed actuator 74 toward the housing 31.

The alignment mechanism 78 is preferably constituted by the manually depressed actuator 74 including a pair of downward depending alignment members 81 on both sides of the vial adapter port 36 towards the drug administration port 34. The alignment members 81 have a lowermost edge 81A transversely directed to the axis of rotation 44.

The stopping mechanism 79 is preferably constituted by the manually depressed actuator 74 including a pair of opposite directly inverted L-shaped arms 82 each formed with an inward facing groove 83 above an abutment endpiece 84 and a vial adapter 86 with a pair of outward radial stoppers 87 for abutment against the abutment endpieces 84 in the initial raised position of the manually depressed actuator 74 to prevent rotation of the vial adapter 86 relative to the housing 31, and in registration with the grooves 83 in a subsequent depressed position of the manually depressed actuator 74 relative to the housing 31.

The manually depressed actuator 74 is initially raised with respect to the housing 31 and its shaft 77 is partially inserted into the throughgoing bore 73 terminating above the radial section 47 so as not to seal same for enabling the mixing flow path between the syringe port 33 and a vial. The fluid control device 70 includes a pin-like plug 88 with a head 89 and a downward depending fluted stem 91. The pin-like plug 88 is initially partially inserted in the male connector 59 such that its head 89 is above the radial section 47 so as not to seal same for enabling the mixing flow path between the syringe port 33 and a vial.

Figure 8:
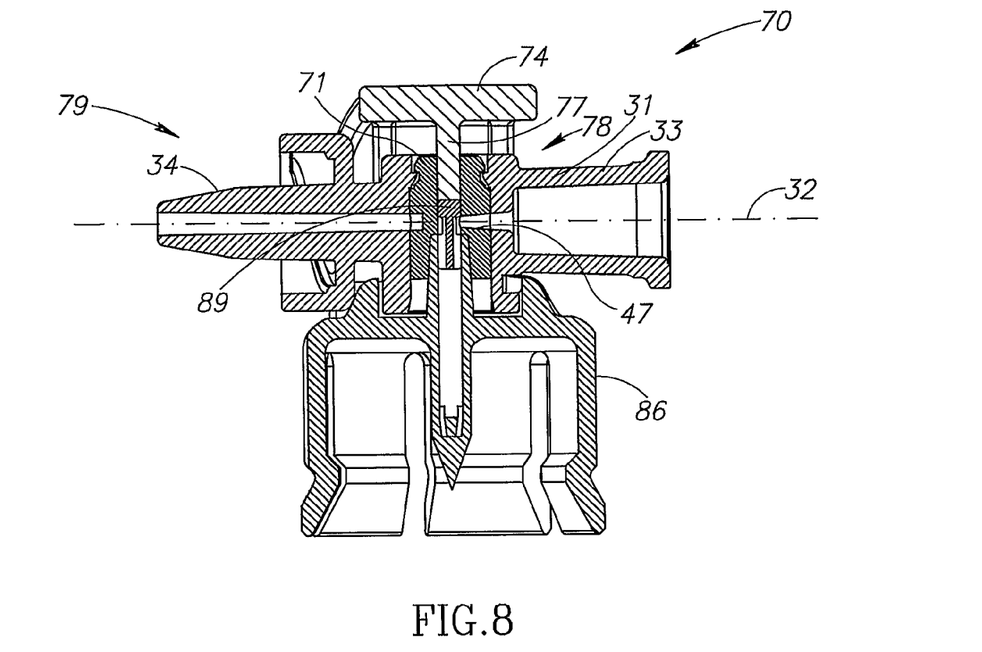
FIG. 8 is a longitudinal cross section of FIG. 5's fluid control device along line B-B in FIG. 5.

FIGS. 8 to 11 show the operation of the fluid control device 70:

FIG. 8 is similar to FIG. 3 insofar that the fluid control device 70 has the vial adapter 86 coupled thereon and the flow control member 71 in its initial mixing flow control position enabling flow communication between a syringe inserted into the syringe port 33 and a vial inserted into the vial adapter 86. The manually depressed actuator 74 is in its raised position relative to the housing 31 and is prevented from rotation with respect thereto by the alignment members 81. The alignment mechanism 78 prevents rotation of the vial adapter 86 relative to the housing 31 and the stopping mechanism 79 prevents vial adapter detachment.

Figure 9:
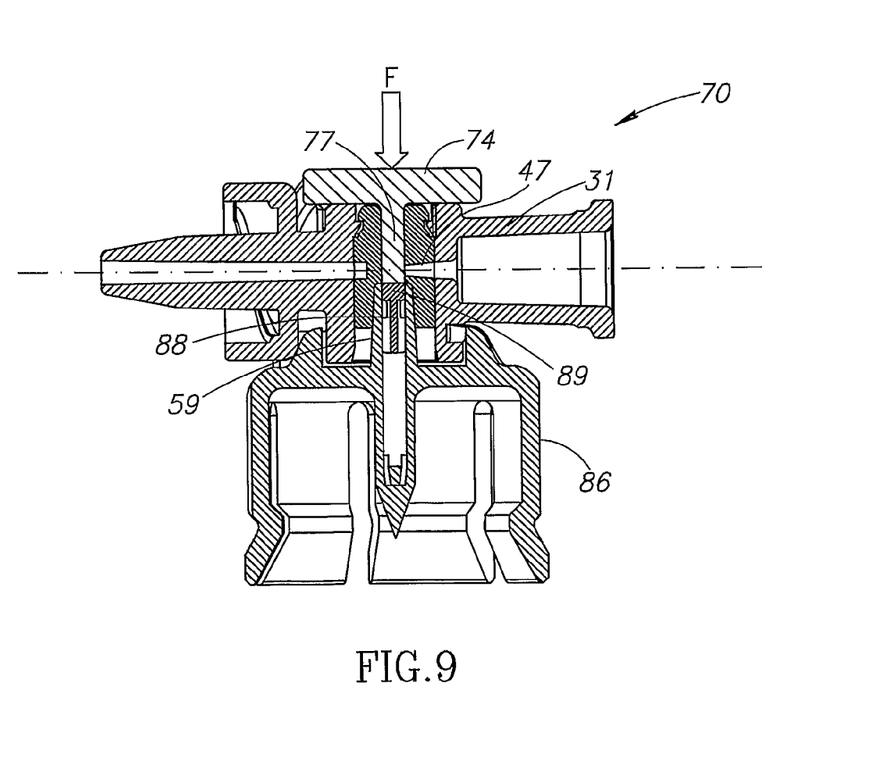
FIG. 9 is a longitudinal cross section of FIG. 5's fluid control device subsequent to actuation of its manually depressed actuator along line C-C in FIG. 6.

FIG. 9 shows depression of the manually depressed actuator 74 under a force denoted by arrow F towards the housing 31 for urging the pin-like plug 88 downwards into the male connector 59 such that the plug's head 89 seals same. The alignment members' lowermost edges 81A are brought into near contact with the housing 31. Depression also causes the actuator's shaft 77 to seal the radial section 47 (see also FIG. 11). Depression also aligns the grooves 83 with the stoppers 87 thereby enabling rotation of the vial adapter 86 relative to the housing 31 for vial adapter detachment without the risk of liquid drug spillage or leakage by virtue of the sealing of the male connector 59 and the radial section 47.

Figure 10:
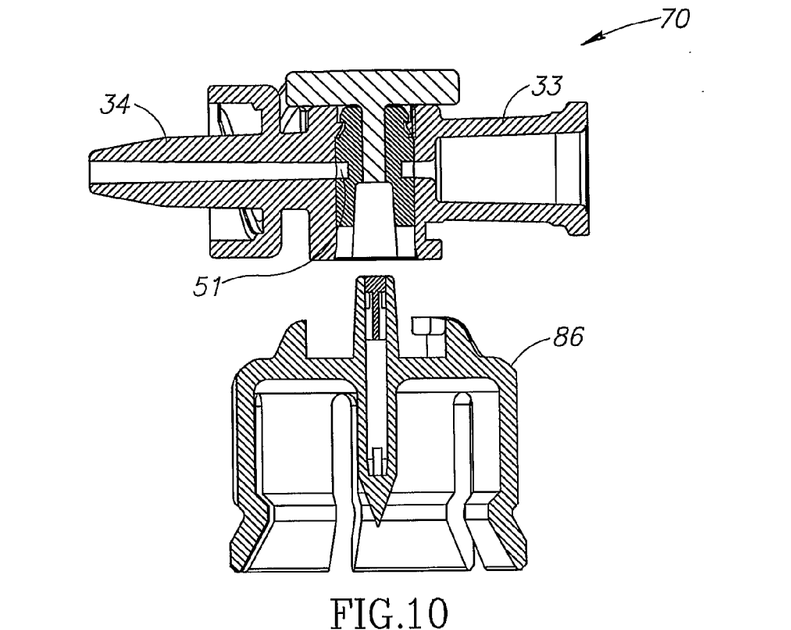
FIG. 10 is a longitudinal cross section of FIG. 5's fluid control device subsequent to vial adapter detachment along line C-C in FIG. 6.
Figure 11:
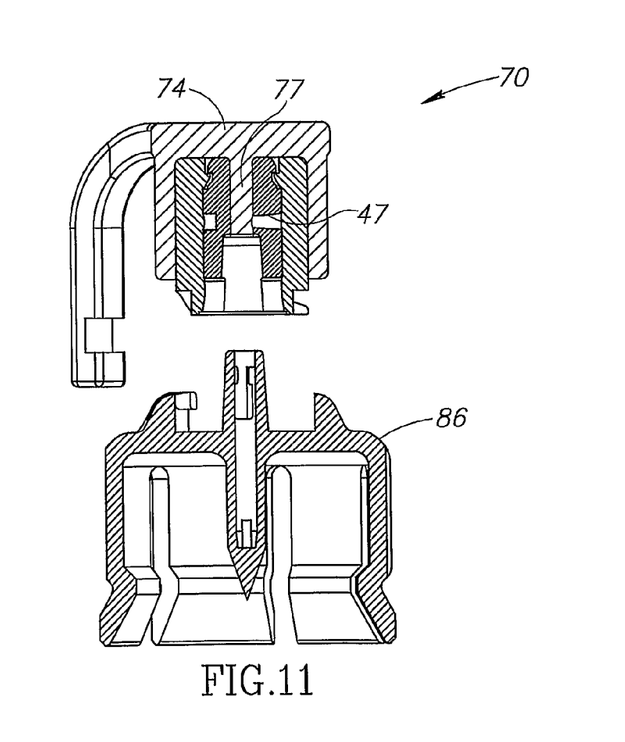
FIG. 11 is a longitudinal cross section of FIG. 6's fluid control device subsequent to vial adapter detachment along line D-D in FIG. 6.

FIG. 10 is similar to FIG. 4 insofar that the fluid control device 70 is ready for liquid drug administration by virtue of the administration flow channel 51 enabling flow communication between the syringe port 33 and the drug administration port 34.

While the invention has been described with respect to a limited number of embodiments, it will be appreciated that many variations, modifications, and other applications of the invention can be made within the scope of the appended claims.

The invention claimed is:

1. A fluid control device for use with a syringe and a vial for administering a liquid drug, the fluid control device comprising:
   (a) a housing having a longitudinal axis, a syringe port and a drug administration port co-directional with said longitudinal axis for correspondingly receiving the syringe and administrating the liquid drug, and a tubular vial adapter port intermediate said syringe port and said drug administration port;
   (b) a flow control member rotatably supported in said vial adapter port about an axis of rotation generally perpendicular to said longitudinal axis, said flow control member including an L-shaped mixing flow channel with a radial section for flow communication with said syringe port in a mixing flow control position and an axial section, said flow control member including a peripheral semi-circular administration flow channel for enabling flow communication between said syringe port and said drug administration port in a subsequent administration flow control position, (c) a vial adapter for telescopically receiving a vial and including an upright tubular male connector and a downward depending tubular cannula for extending into the vial and in flow communication with said male connector, said vial adapter being initially coupled to said housing for sealing insertion of said male connector in said axial section and being rotationally detachable from said housing whereupon rotation of said vial adapter relative to said housing simultaneously rotates said flow control member from said mixing flow control position to said administration flow control position, wherein said flow control member includes an axial extension to said L-shaped mixing flow channel's axial section thereby providing an axial throughgoing bore co-axial with said axis of rotation, and the fluid control device further comprising a manually depressed actuator with a manually depressed head and a downward depending shaft partially inserted into said throughgoing bore in an initial raised position of said actuator relative to said housing, and a pin-like plug with a head and a downward depending fluted stem, the pin-like plug being partially inserted into said male connector for enabling flow communication between said syringe port and the vial in said initial mixing flow control position, the arrangement being such that depression of said manually depressed actuator toward said housing seals said L-shaped mixing flow channel's radial section and causes the downward depending shaft of the manually depressed actuator to contact the head of the pin-like plug to urge the pin-like plug to seal said vial adapter's male connector.

2. The device according to claim 1 and further comprising an alignment mechanism for fixedly aligning said manually depressed actuator relative to said housing and a stopping mechanism for enabling said vial adapter detachment conditional on depression of said manually depressed actuator toward said housing.

3. The device according to claim 2 wherein said alignment mechanism is constituted by said manually depressed actuator including a pair of downward depending alignment members on both sides of said vial adapter port.

4. The device according to claim 3 wherein said alignment members are deployed toward said drug administration port.

5. The device according to claim 2 wherein said stopping mechanism is constituted by said manually depressed actuator including at least one outward radial inverted L-shaped arm with an inwardly directed groove and said vial adapter including a corresponding number of outward radial stoppers for stopping against said at least one L-shaped arm prior to depression of said actuator towards said housing and aligned with said inwardly directed groove subsequent to depression of said actuator towards said housing.

* * * * *